United States Patent

Masubuchi et al.

[11] Patent Number: 5,229,123
[45] Date of Patent: Jul. 20, 1993

[54] ANTIFUNGAL AGENTS

[75] Inventors: Miyako Masubuchi, Yokohama; Toru Okuda; Hisao Shimada, both of Fujisawa, all of Japan

[73] Assignee: Hoffmann-La Roche Inc., Nutley, N.J.

[21] Appl. No.: 947,194

[22] Filed: Sep. 18, 1992

[30] Foreign Application Priority Data

Oct. 9, 1991 [EP] European Pat. Off. ........ 91117164.3

[51] Int. Cl.$^5$ .................. A01N 25/26; A01N 43/16; C07D 311/86
[52] U.S. Cl. .................. 424/408; 424/405; 549/391; 514/455
[58] Field of Search ............ 549/391, 393; 514/455; 424/405, 408

[56] References Cited

U.S. PATENT DOCUMENTS 3,873,714  3/1975  Pfister et al. .................. 424/283

OTHER PUBLICATIONS

Sankawa et al. Heterocyles, vol. 19, #6, 1982, Biosynthesis of Averufin & Sterigmatocystin in Aspergillus.—.
Aoki et al. in Tetrahedron Letters, vol. 32, #36, pp. 4737–4740, 1991 Structure of a Novel Phospholipase C Inhibitor, Vinaxanthone–by *Penicillium vinaceum*.
Cabib, E. et al., Antimicrobial Agents and Chemotherapy, 35(1), 170–173 (1991).

*Primary Examiner*—Thurman K. Page
*Assistant Examiner*—Neil Levy
*Attorney, Agent, or Firm*—George M. Gould; George W. Johnston; Alan P. Kass

[57] ABSTRACT

The compound of the formula

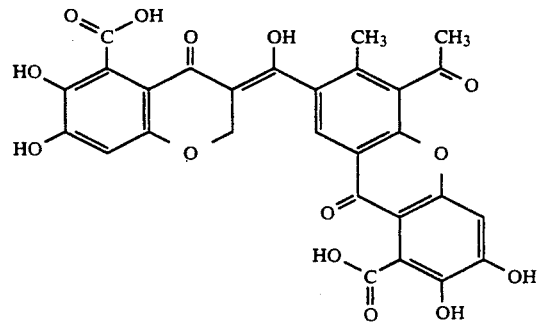

and its tautomer are obtained from cultures of Eupenicillium sp.

The compound has antifungal activity.

12 Claims, No Drawings

ANTIFUNGAL AGENTS

BACKGROUND OF THE INVENTION

The present invention is concerned with a novel compound (hereinafter referred to as Xanthofulvin) of the formula I

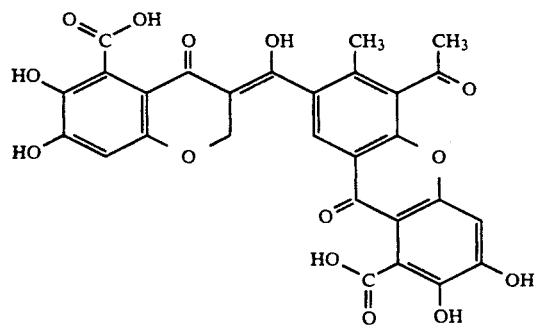

or a salt thereof.

Xanthofulvin also occurs in a tautomeric form of the formula

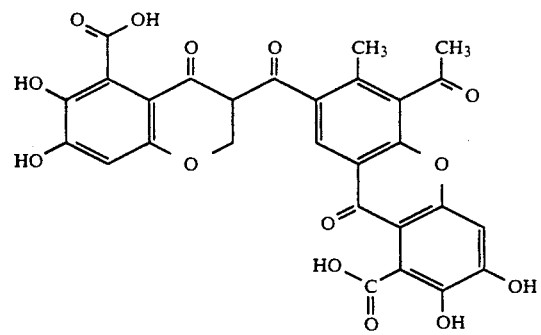

The term Xanthofulvin as used herein refers to both the enol form and the diketo tautomer.

DETAILED DESCRIPTION OF THE INVENTION

The present invention is concerned with a novel compound (hereinafter referred to as Xanthofulvin) of the formula I,

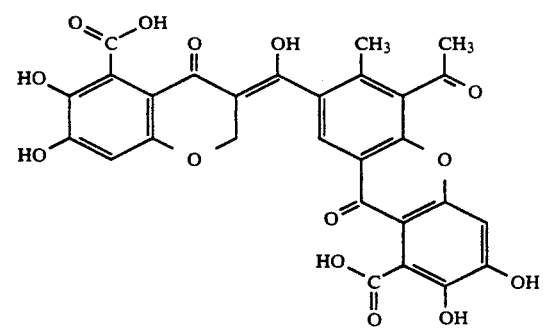

or a salt thereof.

Xanthofulvin also occurs in a tautomeric form of the formula

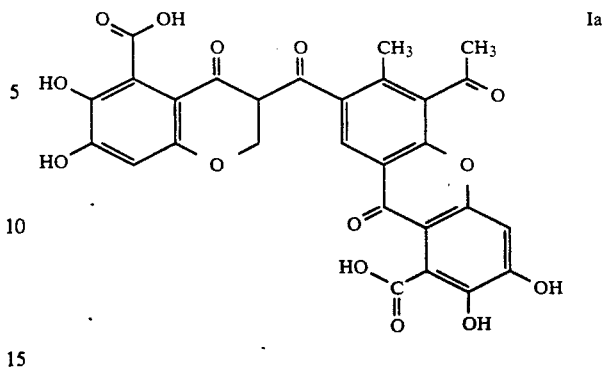

The term Xanthofulvin as used herein refers to both the enol form and the diketo tautomer.

The present invention is also concerned with the use of xanthofulvin to treat or prevent fungal infections in mammals, humans and non-humans, for use as therapeutically active substances, a process for producing Xanthofulvin, a microorganism capable of producing Xanthofulvin, and chitin synthase 2 inhibiting compositions.

Chitin is a linear homopolymer of N-acetylglucosamine. It is commonly found in fungal cells and widely distributed in almost all fungal genera. Chitin is a minor but an essential cell wall component for fungi and does not exist in mammalian cells. Therefore it has been regarded as one of the most attractive targets for antifungals, though very few inhibitors have so far been found. Polyoxins and nikkomycins are well known as chitin synthase inhibitors hut have not yet found clinical use. However, these compounds still draw much attention since the inhibitory activity against chitin synthase is specific and potent. Recently three chitin synthases of *Saccaromyces cerevisiae* were identified (chitin synthase 1, 2 and 3) where chitin synthase 2 (Chs 2) proved to be most critical among the three (N. H. Valdivieso, P. C. Mol, J. A. Shaw, E. Cabib and A. Duran. J. Cell Biol. 114, 101–109 (1991); J. W. Shaw, P. C. Mol, B. Bowers, S. J. Silverman, M. H. Valdivieso, A. Duran and E. Cabib. J. Cell Biol., 114, 111–123 (1991)). Polyoxin D and nikkomycin X were found to inhibit chitin synthase 1 (Chs 1) rather than Chs 2 (E. Cabib. Antimicrob. Agents Chemother., 35, 170–173 (1991))

In accordance with the present invention it has been found that some specific microorganisms produce Xanthofulvin having high Chs 2 inhibiting activity.

The physico-chemical properties of Xanthofulvin obtained as described in the Example given hereinbelow are as follows:

| Appearance: | Yellow crystals |
|---|---|
| Melting point: | 249~251° C. (dec.) |
| Molecular formula | $C_{28}H_{18}O_{14}$ |
| *HRFAB-MS (m/z) (M + H)$^+$: | |
| Calcd.: | 579.0775 |
| Found: | 579.0786 |
| UV $\lambda_{max}$ nm ($\epsilon$): | |
| in MeOH | 239 (33,600), 317 (20,400), 400 (17,800) |
| in MeOH/1N HCl (100:1) | 240 (30,900), 313 (25,000), 365 (17,900) |
| in MeOH/1N NaOH (100:1) | 233 (35,400), 383 (31,000) |
| IR $\nu_{max}$ (KBr) cm-1: | 3430, 1700, 1600, 1480, 1360, 1280 |
| Solubility: | Soluble in DMSO, MeOH Slightly soluble in $H_2O$ Insoluble in n-hexane |
| $^1$H NMR (400 MHz, | 2.37 (3H, s), 2.72 (3H, s), |

| | |
|---|---|
| -continued | |
| CD$_3$OD/CDCl$_3$/DMSO-d$_6$ (2:1:1) used TMS as an internal standard)δ: | 4.67 (2H, br s), 6.43 (1H, s), 6.97 (1H, s), 8.03 (1H, s) |
| $^{13}$C NMR (100 MHz, CD$_3$OD/CDCl$_3$/DMSO-d$_6$ (2:1:1) used TMS as an internal standard)δ: | 16.8, 32.4, 66.6, 102.9, 103.5, 104.9, 110.3, 110.8, 119.2, 120.2, 121.1, 126.6, 130.0, 132.6, 139.1, 139.3, 141.6, 151.0, 152.4, 154.1, 154.7, 156.5, 168.6, 168.8, 171.1, 173.6, 184.4, 202.5 |

*HRFAB-MS: High Resolution Fast Atom Bombardment Mass Spectrometry

According to the process provided by the present invention, Xanthofulvin is produced by cultivating a microorganism belonging to the genus Eupenicillium capable of producing Xanthofulvin under aerobic conditions in an aqueous culture medium and isolating Xanthofulvin from the culture.

The microorganism used in the foregoing process can be any strain (including variants) belonging to the genus Eupenicillium capable of producing Xanthofulvin. Especially preferred strains are Eupenicillium sp. NR7125 as well as variants thereof. Eupenicillium sp. NR7125 was directly isolated from a fruiting body of Marasmius sp. collected in Hachijo-jima Island, Tokyo, Japan, and identified as a strain belonging to the genus Eupenicillium.

The strain denoted as Eupenicillium sp. NR7125 has been deposited with the Fermentation Research Institute, Agency of Industrial Science and Technology, Japan, under the Budapest Treaty on Sep. 30, 1991 as follows: Eupenicillium sp. NR7125 (FERM-BP No. 3588).

The cultural characteristics and the morphological characteristics of Eupenicillium sp. NR7125 (FERM-BP No. 3588) are as follows:

Cultural characteristics

On Czapek-Yeast extract agar (CYA), colonies grew rapidly attaining a diameter of 42–45 mm in 7 days at 25° C., showing floccose in appearance and furrowed in a radiate pattern. Mycelium is white. The conidiogenesis and ascocarp formation were not prominent so that it could not affect the color of the colonies. Exudates or soluble pigments were not produced. Reverse was in pale yellow (Cream Yellow, Munsell, 2.5Y9/4).

On malt extract agar (MEA), colonies grew rapidly to reach 37–40 mm in diameter after 7 days, showing floccose appearance. Mycelium was white. Conidiogenesis was prominent particularly in the central area of the colonies, showing soft blue green (Munsell, 2.5BG7/4). Abundant ascocarps were formed on the surface of the agar. Exudates or soluble pigments were absent. Reverse was pale yellow (Cream, Munsell, 5Y9/2).

On 25% glycerol-nitrate agar (G25N), colonies grew slowly showing compact and velutinous, and reached 16–17.5 mm in diameter in 7 days at 25° C. Conidial production was not prominent. Mycelium was white. Reverse was cream yellow. Pigment in agar was absent.

On CYA at 37° C., colonies grew rapidly attaining a diameter of 29–33 mm.

Morphological characteristics

Conidiophores were born from surface hyphae or aerial hyphae, smooth and thin walled, typically long and slender of 100–250 μm in length. They usually terminated in a verticil of 3–5 phialides (monoverticillate), but sometimes with one or two, rarely three metulae (biverticillate). Metulae were mostly long and divergent, 10–20×2–3 μm. Phialides were ampulliform, 8–12×2–3.5 μm, and abruptly tapered to the apical conidium bearing part. Conidia were most often Subglobose, 2.9–3.6×2.7–3.3 μm with finely roughened to verrucose walls, and born in short chain. Ascocarps were pseudoparenchymatous cleistothecia, 100–250 μm in diam., becoming white to cream, texture sclerotioid but soft, maturing in 3 weeks. Asci were born singly, ellipsoidal, 8.4–11.7×6.8–7.2 μm. Ascospores were hyaline, subspheroidal to broadly ellipsoidal, 2.9–3.5×2.6–3.1 μm, with walls echinulate but without flange.

Ascocarps were sclerotioid and surrounded by pseudoparenchymatous walls. Penicillium-anamorph was readily observed on CYA and MEA. These characteristics clearly indicated that this strain, NR7125 (FERM-BP No. 3588) was included in the genus Eupenicillium Ludwig. Therefore, this strain was identified as Eupenicillium sp. NR7125.

The cultivation in accordance with the process provided by the present invention can be carried out in a culture medium which contains customary nutrients usable by the microorganism being cultivated. As carbon sources there can be mentioned, for example, glucose, sucrose, starch, glycerol, molasses, dextrin and mixtures thereof. Nitrogen sources are, for example, soybean meal, cottonseed meal, meat extract, peptone, dried yeast, yeast extract, cornsteep liquor, ammonium sulphate, sodium nitrate and mixtures thereof. Moreover, there may be added to the culture medium other organic or inorganic substances for promoting the growth of the microorganism and for increasing the production of Xanthofulvin, examples of such substances being inorganic salts such as, for example, calcium carbonate, sodium chloride, phosphates and the like.

The cultivation is carried out under aerobic conditions in an aqueous medium, preferably by submerged fermentation. The cultivation is suitably carried out at a temperature of 20°–35° C., the optimal temperature being 27° C. The cultivation is preferably carried out at a pH of 3 to 9. The cultivation time depends on the conditions under which the cultivation is carried out. In general, it is sufficient to carry out the cultivation for 50~200 hours.

The isolation of Xanthofulvin from the fermentation broth can be carried out according to methods known per se. For example, the mycelium can be separated from the fermentation broth by centrifugation or filtration and Xanthofulvin can be extracted from the filtrate with a water-immiscible organic solvent such as alkanol e.g. n-butanol and esters e.g. ethyl acetate, butyl acetate etc. On the other hand, Xanthofulvin contained in the separated mycelium can be obtained, for example, by extracting the mycelium with a solvent such as aqueous acetone or aqueous methanol, removing the solvent and further extracting the residue with a water-immiscible organic solvent. The thus-obtained solvent phase is dried with a dehydrating agent such as sodium sulphate etc. and then concentrated under reduced pressure. The resulting crude Xanthofulvin can be purified by means of extraction methods, partition methods, precipitation methods, column-chromatographical methods (using silica gel, aluminium oxide etc. as adsorbants) or by means of molecular sieve methods.

Xanthofulvin is isolated as a free acid, but this can be, if required, converted into pharmaceutically acceptable salts such as sodium salt, potassium salt and calcium salt by conventional methods.

Inhibitory activity of Xanthofulvin against Chs 1 and Chs 2 from *Saccharomyces cerevisiae* was measured respectively.

(1) Inhibitory activity against Chs 1

The overproducer employed for Chs 1 was *Saccharomyces cerevisiae* (ura3) harbouring plasmid (CHS1, URA3). The cells were permeabilized with 0.5% digitonin for 15 min at 30° C., followed by treatment with trypsin at the final concentration of 100 µg/ml for 15 min at 30° C. After addition of trypsin inhibitor from soybean, 50 µl of $2.5 \times 10^7$ cells/ml was incubated for 1 hr at 30° C. with 40 µl of assay solution containing 50 mM MES pH 6.5, 5 mM Mg(OAc)$_2$, 32 mM N-acetylglucosamine and 0.1 mM [$^{14}$C]-UDP-N-acetylglucosamine, and 10 µl of sample solution. Reaction was terminated with addition of TCA and cells are collected on the filter and washed with 70% aqueous ethanol containing 0.3M acetic acid. Radioactivity of cells is counted with a liquid scientillation counter. Amount of chitin formed was determined on the basis of radioactivity incorporated into the cells (S. J. Silverman, A. Sburlati, M. J. Slater and E. Cabib. Proc. Natl. Acad. Sci. USA, 85, 4735-4739 (1988)). Inhibitory activity of Xanthofulvin against Chs 1 was shown in Table 1.

(2) Inhibitory activity of Xanthofulyin against Chs 2

Overproducer for Chs 2 was a *Saccharomyces cerevisiae* strain of disrupted Chs 1 gene (chs1:: URA3, leu2 ) with plasmid (CHS2, LEU2). Assay method was the same as the one for Chs 1 described above except for assay solution. Assay solution for Chs 2 contained 30 mM Tris (pH 7.5), 2.5 mM Co(OAc)$_2$, 32 mM N-acetylglucosamine and 0.1 mM [$^{14}$C]-UDP-N-acetylglucosamine (See: Silverman et al. supra). Inhibitory activity of Xanthofulvin was shown in Table 1.

TABLE 1

|  | IC$_{50}$ (µM) | |
| --- | --- | --- |
|  | Chs 1 | Chs 2 |
| Xanthofulvin | >200 | 2.2 |
| polyoxin D | 0.26 | 10.3 |

As shown in the above Table 1, Xanthofulvin has high Chs 2 inhibiting activity. Thus, Xanthofulvin can be used as an antifungal agent, e.g. for the treatment of or prevention of infections with Candida sp. (candidoses).

Acute toxicity of Xanthofulvin is not observed.

The novel Xanthofulvin and salts thereof provided by the present invention can find use as medicaments, for example in the form of unit dose pharmaceutical preparations which contain them or their salts in admixture with an organic or inorganic inert carrier material suitable for enteral application, such as for example water, gelatine, gum arabic, lactose, starch, magnesium stearate, talc, vegetable oils, polyalkylene glycols etc. The unit dose pharmaceutical preparations can be present in solid form, e.g. as tablets, coated tablets, dragees or capsules, hard gelatine or soft gelatine, or in liquid form, e.g. as solutions, syrups, or suspensions.

A dose unit may contain 10 to 200 mg of active ingredient. The daily dosage for an adult can be in the range from 10 to 400 mg and may be varied according to individual requirements which can be determined by those of ordinary skill in the art.

The following Example further illustrates the present invention.

EXAMPLE

Flask fermentation

The spore suspension from well grown slant of Eupenicillium sp. NR7125 (FERM-BP No. 3588) was inoculated into a 500-ml Erlenmeyer flask containing 100 ml of the medium consisting of glucose 2%, glycerol 3%, Polypeptone (Nippon Seiyaku) 0.5%, Yeast extract (Nippon Seiyaku) 0.2%, NaCl 0.3% and CaC03 1%. The flask was shaken at 220 rpm for 3 days at 27° C. Two ml of the resultant culture was each transferred to fifty 500-ml flasks containing the same medium above. The fermentation was conducted on a rotary shaker at 220 rpm at 27° C. After 5 day cultivation, the culture broth was subjected to the isolation procedure described below.

Isolation Procedure

The culture broth (5 liters) was separated into filtrate and mycelium by centrifugation. The culture filtrate (3.2 liters) was extracted with 2 liters of n-butanol at pH 9.0, and the organic layer was discarded. The aqueous layer (3.1 liters) was then extracted with 5 liters of n-butanol at pH 2.0, and the organic layer was concentrated under reduced pressure. The concentrate (24.1 g) was dissolved in 1 liter of methanol and partitioned with 2 liters of n-hexane. The methanol layer was then concentrated to dryness under reduced pressure, and the residue (24 g) was triturated with 50 ml of methanol. After removal of the precipitates by filtration, the filtrate was subjected to a column chromatography on 10.5 liters of Sephadex LH-20 (Pharmacia) using methanol as an eluent. The active fractions were combined and concentrated under reduced pressure to give a yellowish powder which was crystallized from methanol to give 32 mg of Xanthofulvin as yellow crystals.

The following example illustrates a pharmaceutical preparation containing Xanthofulvin provided by the present invention:

EXAMPLE

Tablets each containing the following ingredients were manufactured in the conventional manner per se:

| | |
| --- | --- |
| Xanthofulvin | 100 mg |
| Starch | 26 mg |
| Carboxymethylcellulose calcium | 15 mg |
| Crystalline cellulose | 20 mg |
| Magnesium stearate | 4 mg |
| | 165 mg |

We claim:

1. A compound of formula I

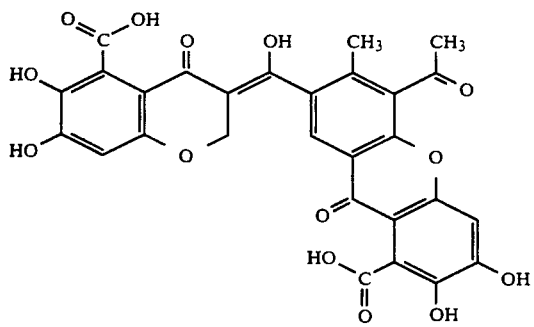

its tautomer or a salt thereof.

2. The tautomer of the compound of claim 1 having the formula

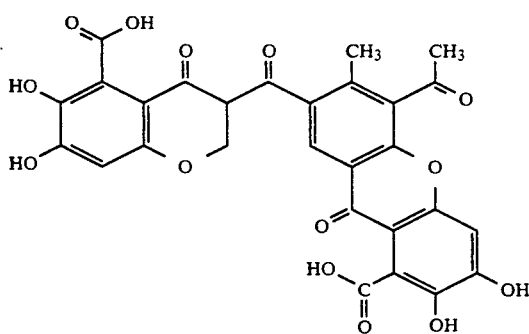

3. A method of inhibiting chitin synthase 2 activity in a mammal in need of inhibiting such chitin synthase 2 activity which comprises administering to a mammal a compound of the formula

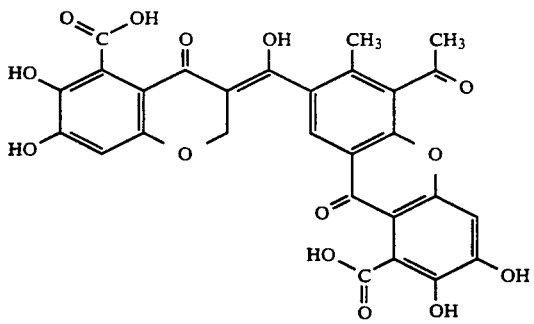

its tautomer or a pharmaceuticaly acceptable salt thereof, in an amount which is effective in inhibiting chitin synthase 2 activity.

4. A pharmaceutical composition comprising a therapeutically effective amount of a compound of the formula

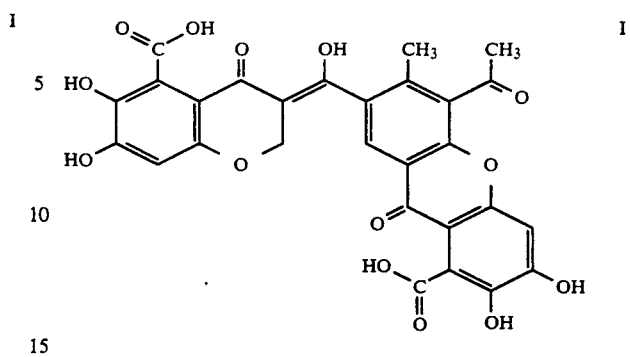

its tautomer or a pharmaceutically acceptable salt thereof, and a therapeutically inert carrier.

5. The pharmaceutical composition of claim 4 wherein the compound is the tautomer of the compound of formula I which has the formula

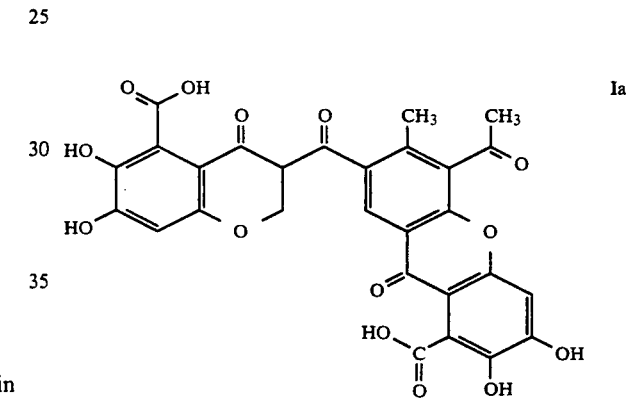

or a pharmaceutically acceptable salt thereof.

6. The pharmaceutical composition of claim 4 wherein the amount of said compound of formula I is about 10 mg to about 400 mg.

7. The pharmaceutical composition of claim 5 wherein the amount of said compound of formula Ia is about 10 mg to about 400 mg.

8. The pharmaceutical composition of claim 4 which is in unit dosage form.

9. The pharmaceutical composition of claim 8 wherein said unit dosage form is selected from the group consisting of tablets, coated tablets, dragees, hard gelatine capsules, soft gelatine capsules, solutions, syrups, and suspensions.

10. The pharmaceutical composition of claim 9 wherein the amount of said compound of formula I in the unit dosage form is from about 10 mg to about 200 mg.

11. A method for treating a mammal having infections caused by fungi which comprises administering to said mammal a compound of the formula

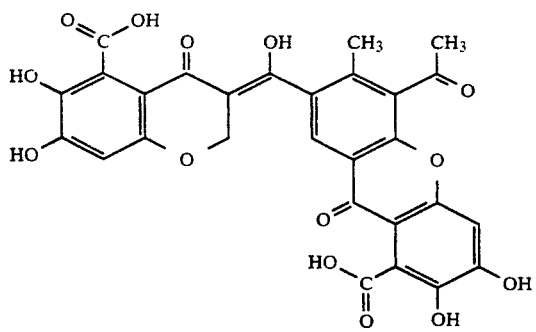

its tautomer or a pharmaceutically acceptable salt thereof, in an amount which is effective in treating infections caused by fungi.

12. A method of prophylaxis against the development of fungal infections which comprises administering to a mammal susceptible to such infections a compound of the formula

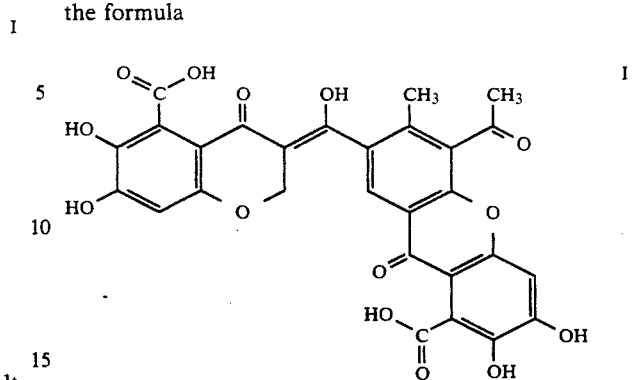

its tautomer or a pharmaceutically acceptable salt thereof, in an amount which is effective as a prophylaxis for fungal infections.

* * * * *